United States Patent [19]

Genna et al.

[11] 4,095,107
[45] June 13, 1978

[54] TRANSAXIAL RADIONUCLIDE EMISSION CAMERA APPARATUS AND METHOD

[76] Inventors: Sebastian Genna, 618 Belmont St., Watertown, Mass. 02172; Sing-Chin Pang, 860 Harrison Ave., Boston, Mass. 02118

[21] Appl. No.: 677,205

[22] Filed: Apr. 15, 1976

[51] Int. Cl.² .............................................. G01T 1/20
[52] U.S. Cl. .................................................. 250/363 S
[58] Field of Search ................ 250/363 S, 445 T, 367, 250/366

[56] References Cited

U.S. PATENT DOCUMENTS

| 3,376,417 | 4/1968 | Keck et al. | 250/363 S X |
| 3,919,556 | 11/1975 | Berninger | 250/363 S X |
| 3,940,625 | 2/1976 | Hounsfield | 250/445 T X |
| 4,010,370 | 3/1977 | Lemay | 250/445 T X |

*Primary Examiner*—Davis L. Willis
*Attorney, Agent, or Firm*—David E. Brook

[57] ABSTRACT

A transaxial radionuclide emission camera apparatus and method for image reconstruction using data collected by the apparatus are disclosed. A significant feature of the camera apparatus is a detector means which is arcuately shaped. For example, a suitable detector means can be formed from an optically continuous, arcuately shaped strip of scintillation material and an array of photodetectors optically coupled to said scintillation material. These photodetectors sense light emitted by the scintillation material in response to absorbed radiation. Collimating means which converge to the center of an arc defined by the detector means are another significant feature. The transaxial camera apparatus and the method disclosed are useful in reconstructing images of the distribution of a source of penetrating radiation contained within a body. A particular example is the three-dimensional reconstruction of the distribution of a radiopharmaceutical in a human brain which is helpful in diagnosing and locating lesions or tumors of the brain. The apparatus can also be used in two-dimensional imaging.

12 Claims, 16 Drawing Figures

TRANSAXIAL RADIONUCLIDE EMISSION CAMERA APPARATUS AND METHOD

BACKGROUND OF THE INVENTION

1. Field of the Invention

This invention is in the field of nuclear medicine and more particularly in the field of radionuclide emission imaging.

2. Description of the Prior Art

These are currently two general modes which use ionizing radiation for diagnosing and delineating diseased tissue within the human body. These are the transmission and emission modes. In the former, penetrating radiation, such as X-rays. is emitted from a source external to a body and transmitted therethrough. In the latter, a radionuclide contained within a body emits penetrating radiation, such as gamma rays, which similarly pass through the body.

In a conventional transmission system, X-rays diverge from a source, penetrate the body to be examined and impinge on a sheet of photosensitive material such as film. The density at each point on the film is representative of the total transmission on the X-rays along a pathway through the body. Increased or diminished attenuation in a small volume along this column is difficult to detect because of the superimposition of the signals from all elementary volumes along a path.

Recently, breakthroughs have occurred with transmission systems which permit three-dimensional image reconstruction of the tissue density distribution of an organ. This makes it possible to image internal structures in three dimensions and to visually display such information. These systems employ mathematical techniques for reconstruction of an image in three dimensions by combining images from two-dimensional scans from different angles, usually referred to as transaxial scans.

One three-dimensional X-ray reconstruction apparatus which has been widely used is known as a "CAT" (computerized axial tomographic) scanner. This scanner is described in a number of United States patents issued in the name of Godfrey Hounsfield, including: U.S. Pat. Nos. 3,778,614; 3,866,047; 3,867,634; 3,881,110; 3,919,552; 3,924,131; and 3,932,757.

In a typical brain scan with the CAT scanner, a patient is positoned with his head cradled in a square gantry. An X-ray tube scans along one side of the gantry coupled to a detector on the opposing parallel side. The entire rectangular structure rotates about an axis through the head. With each 1° rotation of the rectangular gantry, the scanner (X-ray tube and coupled detector) makes a single traverse. Along each scan, a number, $n$, of intensity measurements of a transmitted narrow beam of X-rays are made in contiguous increments and the gantry is ultimately rotated through 180°. Every brain site on a planar section through the brain is thus intersected by the beam n times. Computer reconstruction of the attenuation coefficients of volume elements in the planar section of the brain traversed by the X-rays is accomplished by well known algorithms for the reconstruction of a transaxial section from parallel projections. The scanner actually measures two contiguous planes at a time. Repetitions, following incremental translations of the patient, produces four scans or 8 sections which are usually sufficient to image most adult heads. The family of transectional images constitutes a three-dimensional image of attenuation coefficients for the brain and surrounding tissues.

In typical two-dimensional emission imaging applications, a source of penetrating radiation is administered to the patient. Typically, this consists of a radiopharmaceutical capable of gamma-ray emission. In the so called "rectilinear scanners", gamma-rays emitted and directed along columns defined by lead collimators are recorded by sodium iodide scintillation detectors. Through rectilinear scanning, the detected intensities are transformed into a two-dimensional image which may be displayed on a cathode ray tube or a hard copy such as a film.

So called "scintillation cameras" are capable of imaging an entire organ, such as the brain, without detector motion. In such cameras, a set of parallel lead collimated holes defines a set of columnar trajectories generally perpendicular to the camera face. The detector is constructed to be position sensitive, i.e., the trajectory from whence a gamma-ray originated is identified. This permits direct reconstruction of a two-dimensional projected image by an intensity format on a cathode ray tube and a hard copy such as a film.

While two-dimensional radionuclide emission techniques are widely used, it has been recognized that they suffer from significant drawbacks. Thus, a three-dimensional radionuclide distribution in the interior of an object under examination appears with its details from front to back superimposed. Consequently, the resulting two-dimensional image is often difficult to interpret in that concentrations of activity within small volumes are often not identifiable or adequately pinpointed.

Emission apparatus suitable for three-dimensional image reconstruction has been developed. In one apparatus developed by Kuhl et al., each of four discrete detectors scans rectilinearily along the peripheries of a square gantry. Each detector is collimated so that it can only see gamma-rays directed in a column along its axis. Thus, in each scan, four sets (views) of transaxial parallel projected data are collected for reconstruction. The gantry rotates in increments about an axis perpendicular to the plane of the projections to collect a complete set of views needed for reconstruction, which is done using computerized iterative techniques. See Kuhl, D. E., Edwards, R. Q., Alavi, A., Reivich, M. and Rothenberg, H.; "Radionuclide Computerized Tomography for Brain Study"; Workshop on Reconstruction Tomography in Diagnostic Radiography and Nuclear Medicine, San Juan, Puerto Rico, April 1975. Later embodiments of the Kuhl apparatus include eight detectors positioned contiguously along each scan path. Each detector consists of a sodium iodide scintillation crystal individually collimated and coupled to separate light pipes and photomultipliers.

Additionally, a few proposals have been made for three-dimensional reconstruction using a scintillation camera for detecting gamma-rays from single photoemitters. See Budinger, T. F. and Gullberg, G. T., "Three Dimensional Reconstruction in Nuclear Medicine Emission Imaging," *IEEE Trans* 21, (3), 202(1974); and Keyes, J. W., "Clinical Application of Transaxial Tomography in Nuclear Medicine. Image Processing for 2-D and 3-D Reconstruction from Projection," *OSA*, August, 1975. Each of these uses existing two-dimensional scintillation cameras that are arranged to make measurements in parallel projection geometries similar to Kuhl's. These radionuclide imaging systems have significant limitations. Among these are limited resolution because parallel projections and the planar shape of the detector limits the resolution obtainable by projection of radiation for transaxial reconstruction. The planar shape of the scintillation camera also limits the sensitivity obtainable by projection of radiation for transaxial reconstruction. Additionally, position analysis of the scintillation event as usually employed does not optimize the resolution and generally produces distortions and results in non-uniformities in sensitivity which are known to be as high as 15% in practice.

Regardless of the method of measuring emitted penetrating radiation, the reconstructed transaxial section images will be erroneous unless attenuation by the radionuclide-containing-body is accounted for. A method of correction has been proposed by Kuhl. See Kuhl, D. E., Edwards, R. W., Abass, A., Reivich, M., and Rothenberg, H.: Radionuclide Computerized Tomography for Brain Study (In) Ter-Pogassian, M. M., Phelps, M. E., Brownell, G. L., Ed: *Workshop on Reconstruction Tomography in Diagnostic Radiology and Nuclear Medicine,* San Juan, Puerto Rico, 17–19 April, 1975, University Park Press, New York, 1976. In this work an attenuation correction is applied after reconstruction by correction factors experimentally obtained from a homogeneous cylinder containing a uniform radionuclide distribution. Another method of correction has been proposed by T. Budinger and G. T. Gullberg. See Budinger, T. F. and Gullberg, G. T.: Three-Dimensional Reconstruction in Nuclear Medicine by Iterative Least Square and Fourier Transform Techniques. *Donner Laboratory,* 1974, LBL - 2146. In this case, the projections are approximately corrected for attenuation by geometrical combination of opposing data and from body geometry attenuation corrections before reconstruction. Neither of these correction techniques is entirely satisfactory.

Therefore, an object of the present invention is to provide a method and apparatus for mapping the emission concentration of a radionuclide within a body whereby differences in concentration in small elements in a planar slice can be determined.

Another object is to provide improved sensitivity for transaxial radionuclide sectional imaging.

Another object is to provide improved resolution for transaxial radionuclide sectional imaging.

Another object is to provide a method of position analysis of scintillation camera system whereby resolution and uniformity of detection is improved.

Another object is to provide an improved method of analysis of the data to correct for attenuation.

Another object is to provide a method for direct reconstruction of transaxial images from divergent projections which is capable of analyzing the data "on-line" with its collection.

Another object is to provide a method and apparatus for mapping a radionuclide distribution within a body whereby the distribution is portrayed by cylindrical projections on a cylindrical surface.

DESCRIPTION OF THE INVENTION

The invention relates to a transaxial radionuclide emission camera apparatus and a method for reconstructing images from data collected by the camera apparatus. This transaxial camera apparatus is unique because of its combination of an arcuately shaped detector system with collimators which converge to the center of an arc defined by the detector system.

In a preferred embodiment, the detector system is formed from an arcuately shaped, optically continuous strip of scintillation material, such as thallium activated sodium iodide crystals. This scintillation material is optically coupled, such as by a light pipe, to an array of photodetectors capable of sensing light emitted by the scintillation material in response to absorbed radiation. The light signals sensed by the array of photodetectors are then used, by means of an appropriate algorithm, to reconstruct the desired image.

A preferred collimator means can be formed from an arcuately shaped radiation shield having a plurality of collimating channels therethrough. The channels are oriented to converge to the center of an arc defined by the arcuately shaped detector means.

The camera described herein is, of course, used in combination with other components of an entire system for carrying out image reconstruction. Such systems typically include means for causing relative orbital scanning motion between the body being examined and the detector means as well as means to cause relative linear scanning motion. Both scanning systems can usually be provided by mounting the detector system on an appropriately designed gantry. These systems also include means for generating an image from the light signals detected by the photodetectors, and such means are typically a digital computer programmed with an appropriate algorithm.

The resolution obtainable with the camera apparatus described herein is outstanding due to several factors. The diverging gamma-rays magnify the image on the position detector surface which facilitates spatial resolution of position. Also, optimized analysis of the position of a scintillation by combination of independently determined positions from each photodetector signal is more accurate than established means which employ linear superposition of photodetector signals. Additionally, the surface of an arcuately shaped detector can be made closer to the source of radiation and thus, for the same sensitivity, collimator resolution is less degraded.

Sensitivity for the camera apparatus is also improved. A larger detector surface can be exposed to the emitted radiation which therefore collects more data bearing radiation. Also, the surface of an arcuately shaped detector can be positioned closer to a body being examined and thus, for the same resolution, the collimator holes can be made larger.

Reference to the drawings will hereinafter be made in further describing the invention, wherein.

Figure 1:
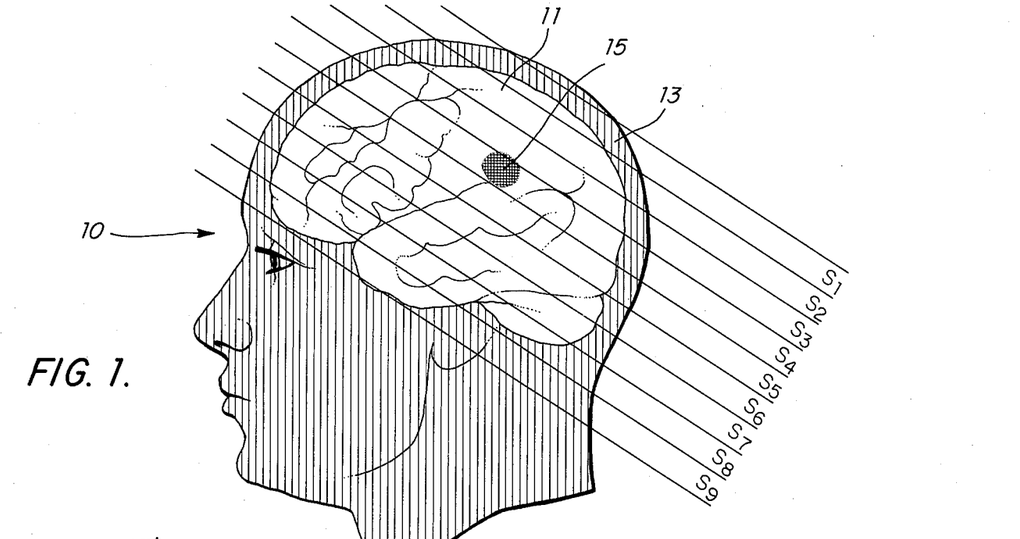
FIG. 1 is a lateral view illustrating a human head containing a brain having a lesion therein and also illustrating a plurality of transaxial slices through the brain.

In the lateral view of human head 10 illustrated in FIG. 1, brain 11 is shown within outer tissues 13. For purposes of illustration, it is assumed that a radio-pharmaceutical has been administered to the patient and is distributed throughout head 10. Radiopharmaceuticals typically contain gamma-emitting radionuclides such as technium-99. As indicated by the shading, outer tissues 13 concentrate the radiopharmaceutical to a much greater degree than brain 11. Certain irregularities, however, such as brain lesion 15, also concentrate high amounts of radiopharmaceuticals as indicated by shading, and this is the basis for radionuclide imaging.

It is desirable to be able to determine the location and delineate the size of brain lesion 15 through scintigraphy. In two-dimensional scintigraphy, this would be done by triangulation from two perpendicular images. In order to reconstruct three-dimensional images of the distribution of radiopharmaceutical in brain 11, brain 11 is divided into a number of transaxial segments or slices, such as slices $S_1$-$S_9$ shown in FIG. 1. Each transaxial slice is imaged from a number of positions around an axis perpendicular to the slice and preferably through 360°. This is usually done by rotating the detector system around the patient. Data from such rotational imaging allows the exact location of irregularities such as in lesion 15 to be pinpointed within a particular transaxial slice. After each transaxial section has been imaged through 360°, the detector system is moved laterally to a new position where another transaxial section is rotationally imaged, again preferably through 360°.

Figure 2A:
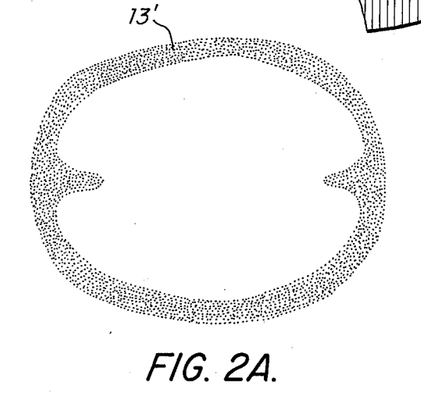
FIG. 2A is a plan view of slice $S_3$ in FIG. 1 and illustrates the distribution of radiopharmaceutical therein.
Figure 2B:
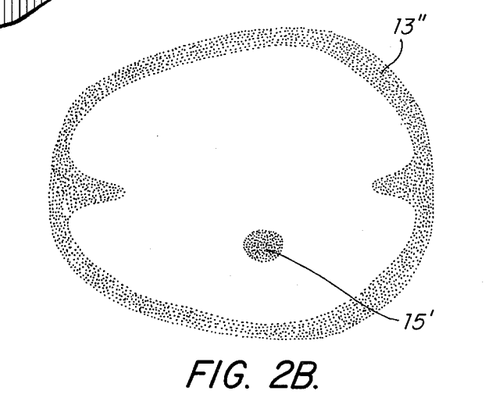
FIG. 2B is a plan view of slice $S_4$ in FIG. 1 and illustrates the distribution of radiopharmaceutical therein.

FIGS. 2A and 2B are plan views of images of transaxial slices $S_3$ and $S_4$, respectively. In the image of transaxial slice $S_3$, a concentrated distribution 13' of radiopharmaceutical is seen at areas corresponding to outer tissues but not at areas corresponding to brain 11, and this is indicated by stippling. Brain lesion 15 does not appear as a concentration of radiopharmaceutical in the image of slice $S_3$. However, in the image of transaxial slice $S_4$, lesion 15 does appear as a concentration 15' of the radiopharmaceutical. Images of transaxial slices $S_3$ and $S_4$, such as those shown in FIGS. 2A and 2B, are constructed from data obtained by rotating a detector for radiation emitted by the radiopharmaceutical in a 360° orbit of head 10 for each of these transaxial slices. The complete set of reconstructed two-dimensional transaxial sections through brain 11 constitutes a three-dimensional image.

Figure 3:
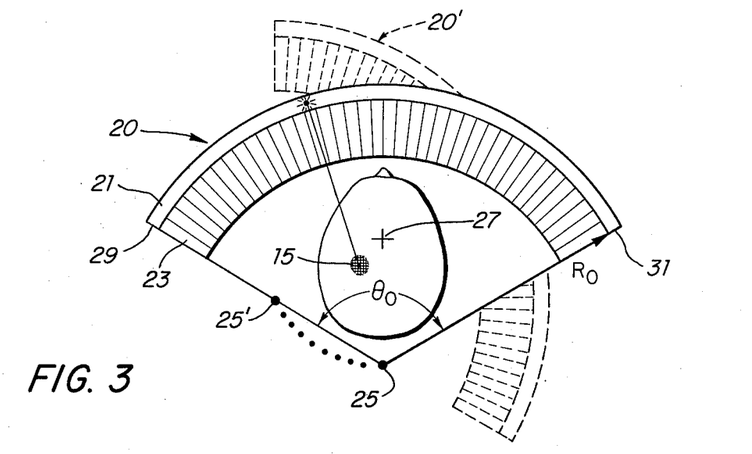
FIG. 3 is a schematic view illustrating the general principles of using an arcuately shaped detector and collimators which converge to the center of an arc defined by the detector in a transaxial radionuclide camera apparatus.

FIG. 3 is a plan view illustrating the general principles of using an arcuately shaped detector system in combination with collimators which converge to the center of an arc defined by the detector to provide a transaxial camera apparatus. Arcuately shaped detector 20 is simply illustrated as being comprised of an arcuately-shaped, optically-continuous scintillation strip 21. Converging collimators 23 are discussed separately in more detail infra, but in general it can be seen that collimators 23 converge to a point 25 which is the center of the arc defined by detector 20. Detector 20 is shown positioned to obtain a first set of data for one transaxial segment. After this set of data has been collected, detector 20 rotates about an axis perpendicular to the plane of the drawing, to another position, such as position 20', where an additional set of data is collected. As detector 20 rotates about the center of rotation 27 to additional positions it can be seen that the center of the arc formed by the detector also changes. Thus, center 25 for detector 20 might change to center position 25' as detector 20 is rotated to position 20'.

Lesion 15 is shown emitting a gamma ray in FIG. 3. The gamma ray passes to collimators 23 wherein it is collimated and transmitted to scintillation strip 21. The precise location for the admission of this gamma ray can be determined as described subsequently.

It is preferable to have the body being examined totally enclosed by the fan-shaped segment defined by the extremities of the arcuately shaped detector and the center of the arc defined by the detector for all views in each transaxial scan. Thus, head 10 in FIG. 3 is completely enclosed by the fan-shaped segment defined by arc center 25 and the extremities 29 and 31 of detector 20. For purposes of illustrating this, a light line has been added connecting these extremities. Enclosing the body being examined in the fan-shaped segment provides the necessary amount of information-bearing radiation. It is particularly preferred to have two arcuately shaped detectory systems which completely surround the body being examined, such as would be the case if two arcuately shaped detectors were positioned in opposition to each other and so that they completely surrounded the body under examination.

As can be appreciated from the detector geometry illustrated in FIG. 3, cylindrical coordinates can best be used in describing the various embodiments of the invention. Therefore, the coordinates generally used herein are R, $\theta$ and Z. In this system, R is the radius of the cylinder, $\theta$ is the angle of the cylinder and Z is the length of the cylinder. Detector 20 is illustrated with a radius R. and an angle $\theta$. The Z dimension extends into the plane of the FIG. 3.

Figures 4, 4A, 5A:
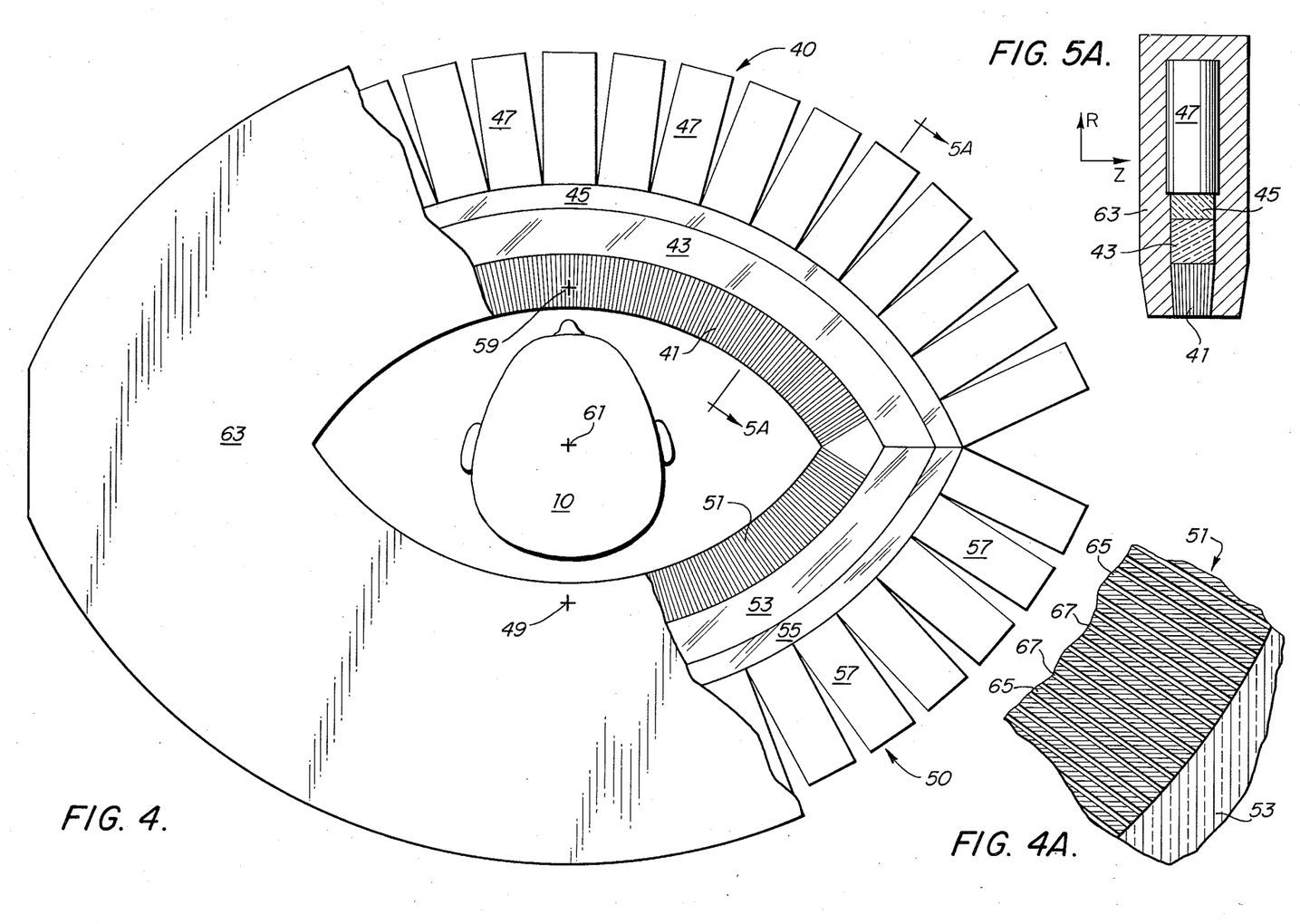
FIG. 4 is a partially cut away plan view of a specific embodiment of a transaxial radionuclide camera apparatus according to this invention.
FIG. 4A is an enlarged view of a section of the collimators shown in FIG. 4.
FIGS. 5A and 5B are cross-sectional views taken along line 5A–5A in FIG. 4 and illustrating two suitable detectors for use in the transaxial radionuclide camera apparatus described herein.

FIG. 4 is a partially cut away plan view of a preferred embodiment of the transaxial camera apparatus described herein. This embodiment contains two oppositely-positioned arcuately shaped position detectors, 40 and 50, which contact each other at their extremities. Because of this, head 10, which represents the body to be examined, is completely enclosed by the detection camera illustrated. This provides increased sensitivity. Detector 40 has a set of converging collimators 41 and, in similar manner, detector 50 has a corresponding set of converging collimators 51.

Arcuately shaped detector 40 is formed from an optically-continuous arcuately-shaped strip of scintillation material 43. Radiation passing through collimators 41 is absorbed by scintillation material 43 which emits light in direct proportion to the amount of radiation energy absorbed at any specific location. Scintillation material 43 is optically coupled by light pipe 45, which can be any transparent material such as glass, and in any number of geometric arrangements. Emitted light is conducted to an array of photodetectors 47, which can be, for example, an array of photomultipliers. Second arcuately shaped detector 50 is similarly formed from arcuately shaped scintillation material 53 joined by light pipe 55 to an array of photodetectors 57.

Photomultipliers 47 and 57 are used in the first and second detectors 40 and 50, respectively, to localize the trajectory of penetrating radiation emitted from radiopharmaceutical contained within head 10. This is usually accomplished by coupling the output of photomultipliers 47 into a digital computer properly programmed with an appropriate algorithm. These aspects of the invention are discussed infra.

Converging collimators 41 and 51 each converge to the center of an arc defined by the detectors 40 and 50, respectively. Thus, the convergence of collimator 41 is to arc center 49 whereas the convergence of collimator 51 is to arc center 59.

The entire transaxial camera system illustrated revolves about an axis of rotation 61 extending into the plane of the drawing (Z axis) and through head 10. In a typical transaxial scan, the camera illustrated is rotated about axis 61 through 180° at predetermined incremental amounts, so that data is collected through 360°.

FIG. 4A is an exploded sectional view of collimator 51 to better illustrate its construction. In FIG. 4A, it can be seen that collimator 51 is formed from a radiation shield material 65, such as lead, having a series of channels 67 extending therethrough. Thus, radiation emitted from body 10 is blocked at all locations except at channels 67. Radiation entering channels 67 is collimated and transmitted to scintillation material 53 which emits an appropriate light signal in response to absorbed radiation energy. As illustrated, it is channels 67 which converge to the center 59 of the arc defined by second detector 50 in FIG. 4.

FIG. 5A is a sectional view of one segment of detector 40 taken along the line 5A—5A illustrated in FIG. 4. The construction of both the converging collimators 41 as well as a single element in arcuately shaped detector 40 can be seen. Converging collimators 41 are joined to scintillation strip 43, which in turn is optically coupled by light pipe 45 to photomultiplier 47. As illustrated, collimator 41 contains channels which converge in the (R, Z) plane, as well as in the (R, $\theta$) plane, as can also be seen in FIG. 4. As previously indicated, all of these elements are enclosed within a radiation shield 63. For purposes of orientation, the R and Z directions are also illustrated.

Figures 5B, 6A:
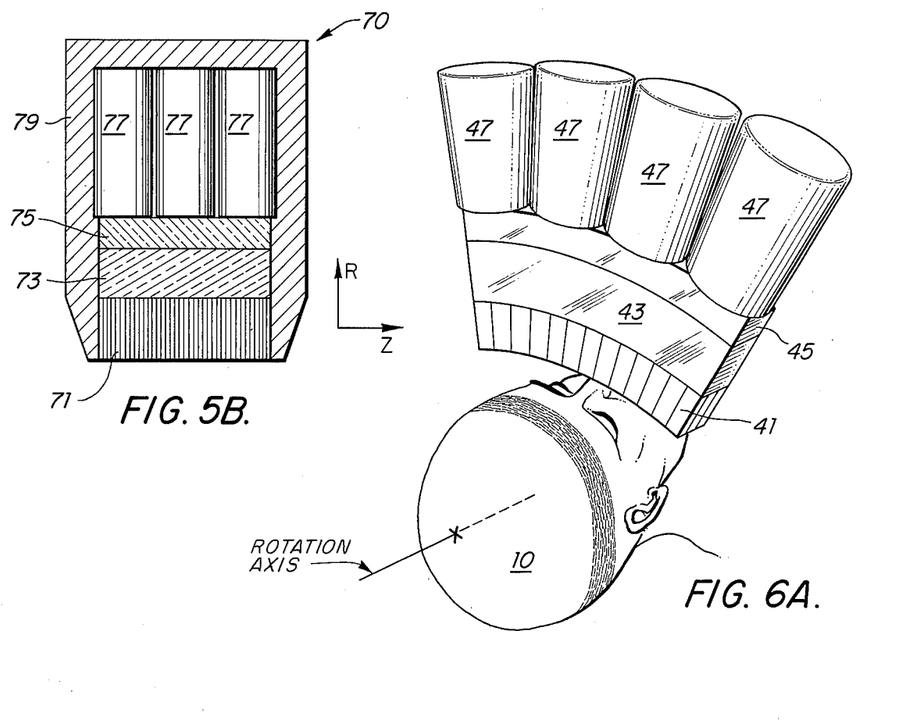
FIG. 6A and 6B are perspective views showing segments of suitable detector systems for obtaining one transaxial scan or plurality of transaxial scans simultaneously, respectively.

FIG. 5B is a sectional view of one segment of an arcuately shaped detector system capable of detecting position in two dimensions, such as in the $\theta$ and Z dimensions. Detector 70 has collimators 71, which are non-converging in the (R, Z) plane. In an (r, $\theta$) plane, collimator 71 converges to a point on the Z axis, as can be seen from FIG. 4.

Detector segment 70 contains scintillation strip 73 and light pipe 75, which have additional length in the Z direction in this system intended to obtain data points in more than one transaxial plane simultaneously. As can be seen, it also contains a plurality of photodetectors 77 which are positioned one over the other in the Z direction, and all of the elements are encased within radiation shield 79.

Figure 6B:
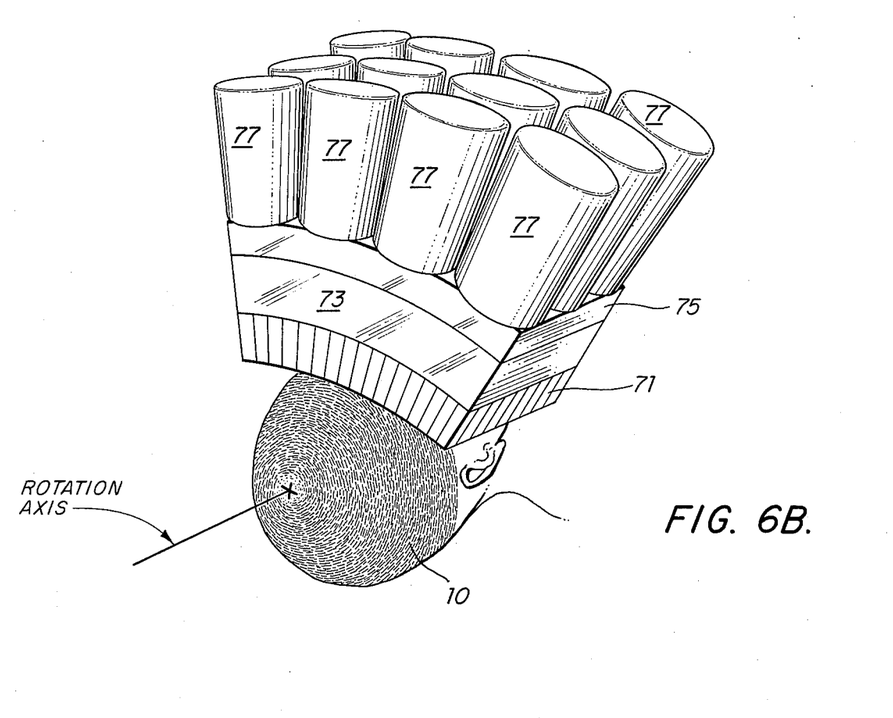

FIGS. 6A and 6B illustrate, respectively, in perspective views, the operation of segments of arcuately shaped detectors capable of operation in one transaxial plane or a plurality of transaxial segments. In FIG. 6A, a segment of detector 40 is illustrated with its axis of rotation extending through head 10. This detector is capable of rotating around head 10 to collect data for one transaxial section, as illustrated by the shaded band on head 10.

The segment illustrated in FIG. 6B is capable of collecting data from multiple transaxial sections simultaneously. As shown by the shading, a much larger area of head 10 can be scanned and imaged at one time using such a detector.

Figure 7:
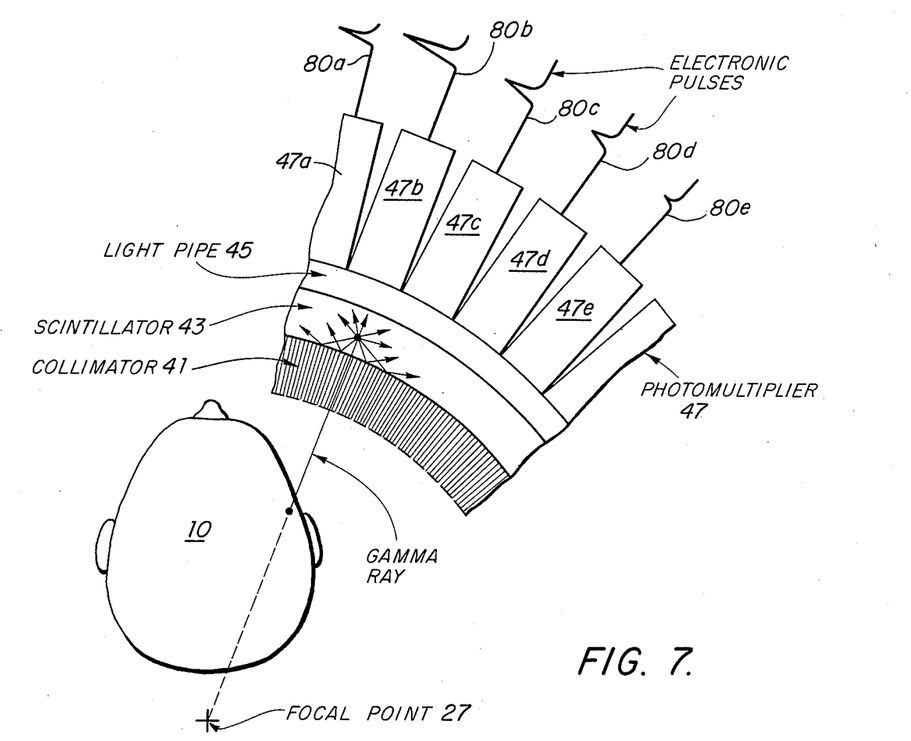
FIG. 7 is a diagrammatic view illustrating the operation for one embodiment of an arcuately shaped detector system suitable for use in the transaxial radionuclide camera systems described herein.

FIG. 7 is a plan view illustrating the operation of a position detection system as described herein. A gamma ray emitted from a site of radiopharmaceutical concentration within head 10 passes through collimator 41 and is absorbed in scintillator 43. In response to the absorbed gamma ray, scintillator 43 emits light isotropically from the absorptive site therein. Scintillator 43 reflects light from all of its boundaries except the one joining light pipe 45 so that all light emitted is contained therein except that transmitted by light pipe 45 to photomultipliers 47. Since scintillator 43 and light pipe 45 are optically-continuous, a light signal is sensed by more than one of the photomultipliers 47. Each of the sensing photomultipliers 47 produces an electronic voltage pulse which is directly proportional to the intensity of light received. Thus voltage pulses 80a...80d are illustrated as having different heights according to the intensity of the light from their respective photomultipliers 47a...47d. It is this distribution of pulse heights emitted by photomultipliers 47 that is used to delineate the exact trajectory of a gamma ray emitted from head 10 and absorbed in scintillation material 43. As illustrated in FIG. 7, the gamma ray could have been emitted from any point along a line connecting focal point or center of the arc 27 to the absorptive site within scintillator 43.

Figure 8:
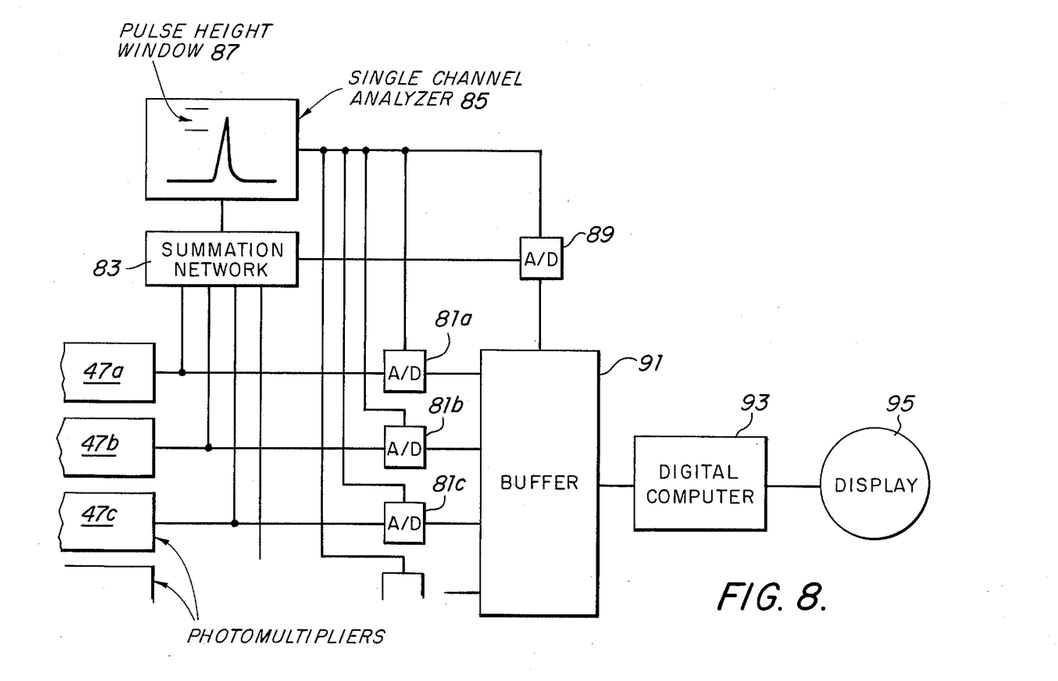
FIG. 8 is a schematic box diagram of a suitable system for three-dimensional reconstruction of scintigraphs from light signals sensed by detector systems useful in the transaxial radionuclide camera systems described herein.

FIG. 8 is a schematic diagram illustrating a suitable electronic network for determining position from the signals generated by photomultipliers 47. The output of photomultipliers 47a, 47b, and 47c, etc., are each fed to analogue-to-digital converters 81a, 81b, and 81c, respectively. In addition, these outputs are also fed to summation network 83, which sums all of the pulses from photomultipliers 47 and feeds the summed result into single channel analyzer 85. Single channel analyzer 85 discriminates against all summed pulses which are not within a preselected pulse height window 87. For signals within the pulse height window 87, a signal from the single channel analyzer 85 is fed to analogue-to-digital (A/D) converters 18a, 81b, 81c, etc., which admits the analogue signals from photomultipliers 47a, 47b, 47c, etc., to analogue-to-digital converters 81a, 81b, and 81c, etc., Digital signals are then fed from A/D converters 81a, 81b, 81c, etc., into buffer 91 and subsequently into a digital computer 93. An analogue pulse from summation network 83 is also fed into A/D converter 89, buffer 91, and digital computer 93. Computer 93 is programmed with an algorithm which allows it to determine the position of the trajectory as illustrated in FIG. 7. Eventually, digital computer 93 has enough data to reconstruct three-dimensional images of the body being examined and the reconstructed image can be transmitted to a display 95, for example, a cathode ray tube. If desired, the reconstructed image displayed can be reduced to hard copy for permanent retention.

The method used to reconstruct three-dimensional images with the data collected using the detector system previously described will now be discussed. This can be done by breaking the method into a series of numbered steps and sub-steps as follows:

1. Penetrating radiation emitted internal to a body by a radionuclide distributed therein is selectively permitted to transmit to an arcuately shaped detector through a plurality of narrow channel apertures in a converging collimator adjacent to said detector. These channels converge to the cylindrical axis of or center of the arc defined by the detector.

2. The detector is a position detector which defines the trajectory of an individual event.

3. In a specific embodiment involving a scintillation detector, the position of a scintillation within the crystal is determined from a digital anaylsis of the pulse height signals from a plurality of photomultipliers optically coupled to the crystal. Position analysis derives from point by point calibration of the detector by the following procedure:

3.1 A narrow gamma ray beam is directed at a point X normal to the face of the scintillator.

3.2 For each gated scintillation (i.e., the summation of the pulse heights from all photomultipliers fall within a prescribed pulse height window) each pulse height is digitized and collected in a computer.

3.3 Some (depending on geometry) of the pulse heights, for example, the five highest, are selected. Each signal is normalized by dividing it by the summation of all pulse heights. The remaining signals are discarded.

3.4 For each position, the normalized pulse height of each photomultiplier is determined to provide a complete set of data for the construction of tables for subsequent determination of position from pulse heights. (The calculation is actually made from the mean of a large number of pulses).

4. The above procedures constitute a calibration. Resulting calibration tables are stored in a computer. Subsequent computer position analysis can be done as follows:

4.1 A set of gated pulses are received in core.

4.2 A group (five in our example) of the highest pulse heights are selected and the remaining pulses discarded. These selected pulses are normalized.

4.3 For each of the normalized signals, tables are consulted to locate the position of the scintillation as prescribed by the phototube and an associated weighting factor.

4.4 A weighted mean of the locations determined by the selected photomultipliers is calculated where the weighting factors depend on the accuracy to which the specified position can be determined from each particular photomultiplier pulse. An event is then recorded as having occurred at the calculated weighted mean and the pulse heights are discarded. The analysis which was demonstrated for a single position variable may also be carried out for two variables.

5. The family of collimator channels which converge to the cylindrical axis of the arcuate detector totally encloses the radioactivity within one or more slices of a body under examination. The data collected for a prescribed time interval from one slice of the body with the detector in a fixed position therefrom comprises a view.

6. A digitized view is obtained by integrating the count events recorded over a number of equal small angular increments of the arc detector, 100, increments, for example. Consequently, the counts deriving from a set of digitized trajectories, say 100 trajectories, in a slice defines a digitized view.

7. Additional digitized views are obtained by rotating the arcuate detector through small angular increments, say 3°, about an axis normal to the slice and parallel to the cylindrical axis of the arcuate detector. A complete family of digitized views consists of all digitized views collected through 360° rotation.

8. By any number of auxiliary methods, not specified in this invention, the contour of each body slice is determined. For example, this may be done during rotation of the detector by mechanical, ultrasonic or transmission techniques 9. The family of digitized views are used to reconstruct an image of a transaxial section of a slice. Such reconstruction is accomplished by modified Fourier Convolution techniques which incorporate corrections for attenuation of the radiation of the body. The digitized data can be reconstructed either by first reorganizing it into a family of digitized parallel trajectory views or directly from the diverging trajectories digitized views obtained with the arcuate detector. In each case two attenuation correction procedures are proposed. The steps are outlined below.

9.1 Parallel Trajector Reconstruction

Data taken from the digitized views can be reorganized into a family of parallel views as proposed by the inventors elsewhere. See Pang, S.C. and Genna S.: A Fourier convolution fan-geometry reconstruction algorithm: Simulation studies noise propagation, and polychromatic degradation. (In) *Workshop on Reconstruction Tomography in Diagnostic Radiology and Nuclear Medicine,* San Juan, Puerto Rico, 17–19 April, 1975, University Park Press, New York, 1976. The sectional image can be reconstructed by usual convolution and back projection procedures. See Budinger, T. F. and Gullberg, G. T.: Three dimensional reconstruction in nuclear medicine by iterative least square and Fourier transform techniques. See Ramachandran, G. N. and Lakshminarayana, A. V.: Three-dimensional reconstruction from radiographs and electron micrographs: A publication of convolution instead of Fourier Transforms. *Proc. Nat. Acad. Sci.* USA 68: 2236-2240, 1971. See Shepp, L. A. and Logan, B. F.: Reconstructing interior head tissue from X-ray transmissions. *IEEE Transactions of Nuclear Science,* NS 2;:228-236, 1974. Subsequently, attenuation is corrected for by dividing the reconstructed image value at a point by the effective transmission of a gamma-ray at that point. This effective gamma-ray transmission is the average of the transmission calculated for each view over all views. For each view the transmission from a point is determined from auxiliary transmission reconstruction or approximately from measured body contour.

Figure 9:
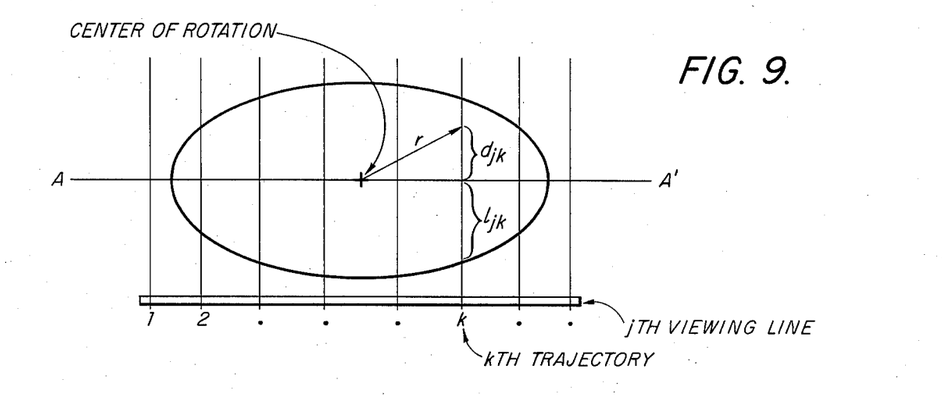
FIGS. 9-11 illustrate suitable reconstruction techniques.

A second method of reconstruction which incorporates a different attenuation correction is explained by reference to FIG. 9. On each view a line AA' is drawn parallel to the viewing line and passing through the center of rotation. A set of trajectory distances between AA' and the boundary of the body section is found. In FIG. 9, one trajectory distance $l_{jk}$ corresponding to the $j^{th}$ view and the $k^{th}$ trajectory is shown. For each $l_{jk}$ the transmission $T_{jk}$ from auxiliary measurements is calculated. Then the data at the trajectory is divided by $T_{jk}$. The complete set of corrected data constitutes a corrected view. Corrected views are convoluted in a usual manner. See "Pang and Genna, Puerto Rico, Op. cit. supra."

(a) Following convolution the data is back projected into the transaxial section line by line again in the usual manner. See "Pang and Genna, Puerto Rico, Op. cit. supra."

(b) However, each point along the line is further corrected for attenuation. FIG. 9 illustrates this correction for a particular point $\vec{r}$. The distance from the point $\vec{r}$ on the trajectory to AA' is obtained and the transmission $T'_{jk}$ from auxiliary measurements is calculated. The back projected data at the point is divided by the transmission $T'_{jk}$. The image is obtained by summation of the corrected back projections over all views.

9.2 Diverging Trajectory Reconstruction

Figure 10:
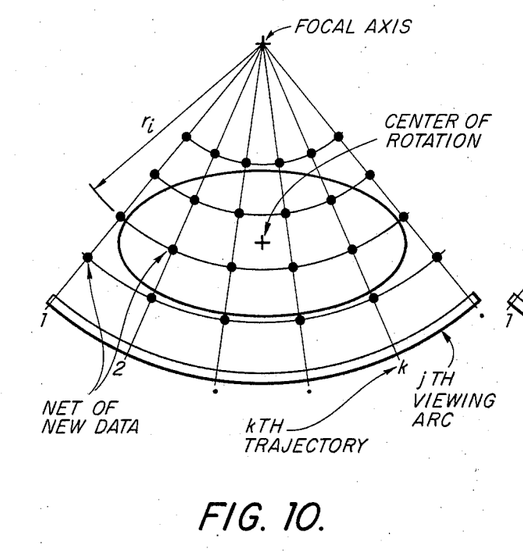

The sectional image is reconstructed from divergent trajectories by a convolution procedure followed by back projection. The procedure is as follows:

Each datum point in each view is replaced by a number of data points located at different prescribed radial distances, $\vec{r}_1, \vec{r}_2 \ldots \vec{r}_i$, from the focal point as shown in FIG. 10. Each new datum in a digitized view is generated by linear superposition of all original data in the same view wherein the weighting coefficients are dependent on the radial distances $\vec{r}_i$. The complete set of new data forms a "net view." For a more complete description, see Pang and Genna, Puerto Rico, Op. cit. supra and Pang and Genna, OSA, Op. cit. supra. For each net view encompassing a transaxial section the contribution to the image at any point thereon is found by extrapolation from the four closest surrounding data in the net view. The summation of the contributions from all net views to that reconstructed point gives the value of the image element at that point.

Subsequently, attenuation is corrected for by dividing the reconstructed image value at a point by the effective transmission of a gamma-ray at that point. This effective gamma-ray transmission is the average of the transmission calculated for each view over all views. For each view the transmission of a point to the detector is determined from auxiliary transmission reconstruction or approximated from measured body contour.

A second method of reconstruction which incorporates a different attenuation correction is explained by reference to FIG. 11. On each view an arc AA' of a circle centered on the focal point of the arcuate detector is drawn, such that it passes through the center of rotation. A set of trajectory distances from AA' to the boundary of a body section is found. In FIG. 10, one trajectory distance $l_{jk}$ corresponding to the $J^{th}$ view and the $k^{th}$ trajectory is shown. For each $l_{jk}$ the transmission $T_{jk}$ is calculated from auxiliary measurements. Then the data at the trajectory is divided by $T_{jk}$. The complete set of corrected data constitutes a corrected digitized view.

Figure 11:
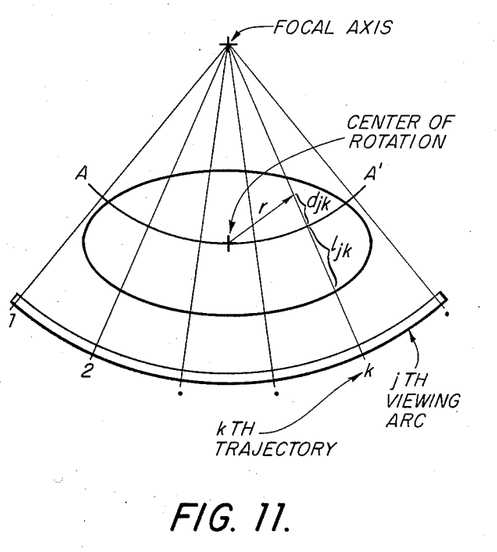

Each datum point in each view is replaced by a number of data points located at different prescribed radial distances, $\vec{r}_1, \vec{r}_2 \ldots \vec{r}_i$, from the focal point as shown in FIG. 11. Each new datum is generated by linear superposition of all corrected data from the same view wherein the weighting coefficients are dependent on the radial distances $\vec{r}_i$. The complete set of new data forms a "net view," as described previously. Each point is further corrected. FIG. 11 illustrates this correction for a particular point $\vec{r}$. The distance from the point $\vec{r}$ on the trajectory to AA' is obtained and the transmission $T_{jk}$ from auxiliary measurements is calculated. The data at the point is divided by the transmission $T_{jk}$. For each net view encompassing a transaxial section the contribution to the image at any point thereon is found by extrapolation from the four closest surrounding data in the net view. The summation of the contributions from all net views to that reconstructed point gives the value of the image element at that point.

Figure 12:
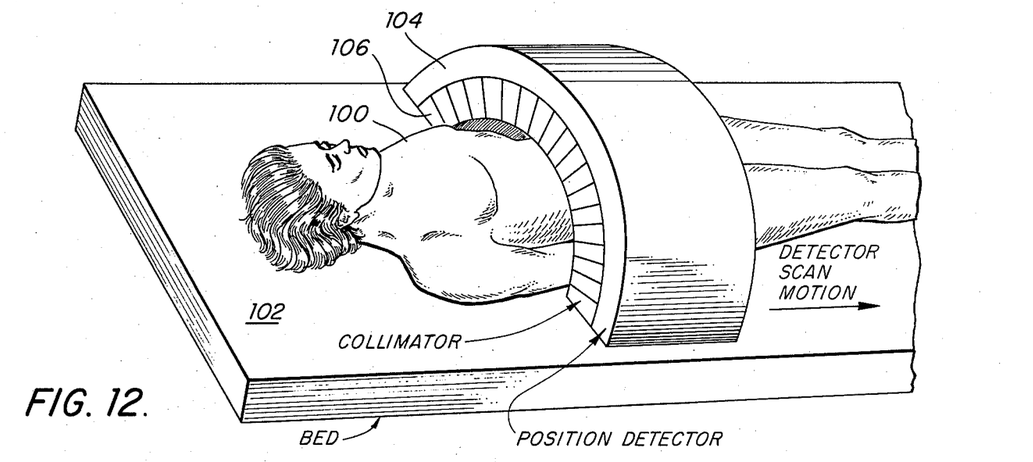
FIG. 12 is a perspective view illustrating how the transaxial radionuclide camera apparatus described herein can be used in reconstructing two-dimensional images of the distribution of a radiopharmaceutical in a body.

FIG. 12 is a perspective view illustrating the use of an arcuately-shaped emission camera detector system, as described herein, for two-dimensional imaging. A patient 100 is shown resting on a bed 102. Arcuately-shaped position detector 104 and converging collimators 106 are positioned over the patient so that gamma rays projected cylindrically outwardly from the patient are detected. Both the position detector 104 and converging collimators 106 are illustrated simply for purposes of convenience, but it should be understood that each of these are similar to the specific embodiments described supra. The image is the two-dimensional projection of the radionuclide distribution on the cylindrical surface and can be presented for visual display on a cathode ray tube, etc., by unfolding the surface onto a plane. This embodiment is capable of producing a static view, but can also be used to image regions larger than the detector by simply scanning the detector in the longitudinal direction.

It is realized that systems capable of detecting radiation can be either one-dimensional position detectors in the form of an arc or two-dimensional position detectors in the form of a cylinder as shown. The term "arcuately shaped," as used herein, is intended to include both devices.

Also, the terminology "center of the arc" has been used, although the center is really the center of a circle of which the arc is a part. The simplification in terminology was done for convenience, and is not intended to limit the invention in any manner.

It will be recognized by those skilled in the art that there are many equivalents to the specific embodiments of the apparatus illustrated herein, as well as to the specific manipulative steps of the method described. For example, although digital position determminations has been emphasized herein, analogue position detection could also be used. Another example is, that although the diverging reconstruction method was described in terms of an emission system, it is also applicable to an x-ray system in which case the common point is the x-ray source.

What is claimed is:

1. In an apparatus for imaging distributions of a source of penetrating radiation contained within a body and wherein said apparatus includes means for collimating emitted radiation and means for detecting the trajectory of emitted, collimated radiation:

the improvement wherein said means for detecting is arcuately shaped and said means for collimating converges to the center of an arc defined by said means for detecting.

2. An improvement of claim 1 wherein said means for detecting comprises an arcuately-shaped, optically-continuous scintillation strip optically coupled to an array of photodectors.

3. An improvement of claim 2 wherein said means for collimating comprises a radiation shield having channels therethrough, said channels converging to the center of the arc defined by said arcuately-shaped optically-continuous scintillation strip.

4. A radionuclide camera for detecting distributions of a source of penetrating radiation contained within a body, said apparatus comprising, in combination:
   a. an optically-continuous, arcuately-shaped strip of scintillation material, said scintillation material being one which emits light in response to absorbed radiation energy;
   b. means for collimating radiation emitted from said source, said means converging to the center of an arc defined by said arcuately-shaped scintillation strip;
   c. an array of photodetectors positioned adjacently to said scintillation strip; and
   d. means for optically coupling said scintillation strip to said photodetectors whereby light emitted by said scintillation strip in response to radiation energy absorbed therein is transmitted to said photodetectors.

5. An apparatus of claim 4 wherein said means for collimating comprises a radiation shield having a plurality of collimating channels therethrough, said channels converging to the center of an arc defined by said arcuately-shaped strip of scintillation material.

6. An apparatus of claim 5 wherein said array of photodetectos is a plurality of photomultipliers.

7. An apparatus of claim 6 wherein said means for optically coupling comprises a light pipe.

8. An apparatus of claim 4 wherein said array of photodetectors extends in the $\theta$ direction when the cylindrical coordinates, R, $\theta$ and Z, are used to describe the detector.

9. An apparatus of claim 4 wherein said array of photodetectors extends in both the $\theta$ and Z directions when the cylindrical coordinates, R, $\theta$ and Z, are used to describe the detector.

10. An apparatus for three-dimensional reconstruction of images of the distribution of a source of radioactivity contained within a body, comprising, in combination:
    a. means for detecting emitted radiation, said means including a detector having an arcuate shape, an optically continuous scintillation strip which emits light in response to absorbed radiation, converging collimating means for collimating emitted radiation prior to its absorption in the scintillation material, and an array of photodetectors for sensing light intensities emitted from said scintillation material in response to radiation absorbed therein;
    b. means to cause relative orbital scanning motion between said body and said means for detecting;
    c. means to cause relative linear scanning motion between said body and said means for detecting; and
    d. means for generating a three-dimensional image of the distribution of said source of radiation contained within said body from the light intensities sensed by said array of photodetectors.

11. An apparatus of claim 10 wherein said means for generating includes a digital computer.

12. A method for reconstructing images of the distribution of radiation emitted from a radio-phramaceutical contained within a body, comprising:
    a. collimating said emitted radiation onto an arcuately-shaped strip scintillation material;
    b. sensing light emitted by said scintillation material with a plurality of photodetectors;
    c. converting the light intensities sensed into electrical signals representative of said light intensities; and,
    d. generating an image of the distribution of radiation emitted from said electrical signals.

* * * * *